United States Patent [19]

Clarke et al.

[11] Patent Number: 5,222,495
[45] Date of Patent: Jun. 29, 1993

[54] NON-INVASIVE BLOOD ANALYSIS BY NEAR INFRARED ABSORPTION MEASUREMENTS USING TWO CLOSELY SPACED WAVELENGTHS

[75] Inventors: Richard H. Clarke, Big Sky, Mont.; Qian Wang, Boston, Mass.

[73] Assignee: Angiomedics II, Inc., Newton, Mass.

[21] Appl. No.: 930,070

[22] Filed: Aug. 14, 1992

Related U.S. Application Data

[63] Continuation-in-part of Ser. No. 649,477, Feb. 1, 1991, which is a continuation-in-part of Ser. No. 474,344, Feb. 2, 1990, Pat. No. 5,054,487.

[51] Int. Cl.$^5$ ............................................. A01B 5/00
[52] U.S. Cl. .................................... 128/633; 356/41; 118/664
[58] Field of Search .......................... 128/633–634, 128/664–666; 356/41

[56] References Cited

U.S. PATENT DOCUMENTS

| | | | |
|---|---|---|---|
| 3,463,142 | 8/1969 | Harte | 128/2 |
| 3,638,640 | 2/1972 | Shaw | 128/2 |
| 3,958,560 | 5/1976 | March | 128/2 |
| 4,014,321 | 3/1977 | March | 128/2 |
| 4,169,676 | 10/1979 | Kaiser | 356/39 |
| 4,202,339 | 5/1980 | Wirtzfield et al. | 128/419 |
| 4,223,680 | 9/1980 | Jobsis | 128/633 |
| 4,350,163 | 9/1982 | Ford, Jr. et al. | 128/633 |
| 4,408,880 | 10/1983 | Tsuji et al. | 356/338 |
| 4,655,225 | 4/1987 | Dahne et al. | 128/633 |
| 4,704,029 | 11/1987 | Van Heuvelen | 356/39 |
| 4,714,080 | 12/1987 | Edgar, Jr. et al. | 128/666 |
| 4,785,814 | 11/1988 | Kane | 128/634 |
| 4,796,636 | 1/1989 | Branstetter et al. | 128/633 |
| 4,840,179 | 6/1989 | Ullrich | 128/633 |
| 4,854,699 | 8/1989 | Edgar, Jr. | 356/41 |
| 4,882,492 | 11/1989 | Schlager | 356/41 |
| 4,901,728 | 2/1990 | Hutchison | 128/633 |
| 4,975,581 | 12/1990 | Robinson et al. | 128/633 |
| 5,007,423 | 4/1991 | Branstetter et al. | 128/633 |
| 5,054,487 | 10/1991 | Clarke | 128/633 |
| 5,070,874 | 12/1991 | Barnes et al. | 128/633 |
| 5,086,229 | 2/1992 | Rosenthal et al. | 128/633 |

FOREIGN PATENT DOCUMENTS

| | | |
|---|---|---|
| 0160768 | 11/1985 | European Pat. Off. |
| 0282210 | 9/1988 | European Pat. Off. |
| 0282234 | 9/1988 | European Pat. Off. |
| 0404562 | 12/1990 | European Pat. Off. |
| WO90/07905 | 7/1990 | PCT Int'l Appl. |

(List continued on next page.)

OTHER PUBLICATIONS

Giangiacomo et al., "Predicting Concentrations of Individual Sugars in Dry Mixtures by Near-Infrared Reflective Spectrascopy," Journal of Food Science, vol. 46, pp. 531–534.

Mendelson et al., "Spectrophotometric Investigation of Pulsatile Blood Flow for Transcutaneous Reflectance Oximetry," Adv. Exp. Med. Biol., vol. 159, pp. 93–102.

(List continued on next page.)

Primary Examiner—Kyle L. Howell
Assistant Examiner—Robert L. Nasser, Jr.
Attorney, Agent, or Firm—Thomas J. Engellenner

[57] ABSTRACT

Systems and methods for non-invasive blood analysis are disclosed in which blood is illuminated at a plurality of discrete wavelengths selected from the near infrared spectrum. Measurements of the intensity of transmitted or reflected light at such wavelengths are taken, and an analysis of transmittance or reflectance ratios for various wavelengths is performed. Changes in the ratios can be correlated with specific near infrared (IR) absorption peak for the analyte which varies with concentration of the analyte (the data wavelength) and the a second (reference) wavelength being sufficiently removed from the first so that measurements of light absorption at this second wavelength are relatively insensitive to the concentration of the analyte and yet the second wavelength is sufficiently close to the first wavelength to minimize interference from scattering effects and the like. Typically, the window bracketing these closely spaced wavelengths will be less than about 300 nm and preferably less than about 60 nm wide and, in some instances, more preferably less than about 30 nm wide.

20 Claims, 5 Drawing Sheets

FOREIGN PATENT DOCUMENTS

WO91/11136  8/1991  PCT Int'l Appl.
2033575  5/1978  United Kingdom.
2075668  11/1981  United Kingdom.

OTHER PUBLICATIONS

Osborne, "Applications of NIR in the Baking Industry," Anal. Proc., vol. 20, pp. 79–83.

Peuchant et al., "Determination of Serum Cholesterol by Near-Infrared Reflectance Spectrometry," Anal. Chem. vol. 59, pp. 1816–1819.

Polanyi et al., "In Vivo Oximeter with Fast Dynamic Response," The Review of Scientific Instruments vol. 33, No. 10, pp. 1050–1054.

Steinke et al., "Reflectance Measurements of Hematocrit and Oxyhemoglobin Saturation," the American Physiological Society, pp. H147–H153.

Wilson et al., "Noninvasive Detection of Skeletal Muscle Underperfusion with Near-Infrared Spectroscopy in Patients with Heart Failure," Circulation vol. 80, No. 6, pp. 1668–1674.

NON-INVASIVE BLOOD ANALYSIS BY NEAR INFRARED ABSORPTION MEASUREMENTS USING TWO CLOSELY SPACED WAVELENGTHS

REFERENCE TO RELATED APPLICATIONS

This application is a continuation-in-part of U.S. application Ser. No. 649,477, filed Feb. 1, 1991, which is a continuation-in-part of U.S. application Ser. No 474,344 filed Feb. 2, 1990, now U.S. Pat. No. 5,054,487 issued Oct. 8, 1991, both of which are incorporated herein by reference.

BACKGROUND OF THE INVENTION

The technical field of this invention is material analysis and, in particular, the invention relates to the detection and quantification of analytes in materials by measuring the absorption of near infrared light.

Material analysis, especially the analysis of liquid materials for the presence of solutes, can be a tedious and complex task. In many instances, it would be more desirable to be able to analyze materials quickly, easily and non-invasively. One example of such an application is blood analysis.

Treatment of many medical disorders, such as diabetes and other hormonal or metabolic disorders, requires accurate blood analysis. Additionally, in some situations, repeated or even continuous blood monitoring is desirable, for example, when monitoring drug dosage changes or variations in metabolic factors, such as glucose or cholesterol.

Conventionally, blood is analyzed by withdrawing a sample from the body of a subject and examining it, using one or more techniques, such as immunoassays, activity assays, chromatographic assays and spectrophotometric assays. These conventional methods suffer from several common disadvantages. One such disadvantage is that these tests are invasive and raise the risk of patient infection and discomfort. Also, such tests can be time-consuming. This time delay between when the blood is drawn and when the analysis is completed provides a window during which the subject's blood content may have changed, possibly leading to erroneous test results. A further disadvantage to conventional blood testing techniques is that the people drawing and testing the blood sample are put at risk for exposure to infectious disease agents.

Accordingly, it is the object of the present invention to provide an analytic apparatus for non-invasively, quickly and continuously detecting and quantifying analytes in a blood sample.

It is another object of this invention to provide a method and apparatus for non-invasive detection of blood-glucose levels but which avoids the problems of non-continuous test results, subject discomfort and potential technician exposure to infectious agents.

SUMMARY OF THE INVENTION

Systems and methods for non-invasive blood analysis are disclosed in which a blood sample is non-invasively illuminated through a patient's tissue, such as the skin, at a plurality of wavelengths, including a reference and a data wavelength, for a target analyte. These wavelengths are preferably selected from the near infrared spectrum, and are also preferably closely spaced to each other in order to minimize interference from other solutes in the blood. Non-invasive measurements of the absorption of light at such wavelengths are taken (e.g., by measuring reflectance or transmittance), and a non-invasive analysis of absorption ratios is performed for various sets of these wavelengths. Changes in the detected reflectance or transmittance ratios are then correlated with specific material properties, such as the concentration of glucose, urea or cholesterol in a subject's circulatory system.

One problem in obtaining reliable blood-analyte data is that the light impinged on the sample is scattered by various local properties of the subject. However, by performing a ratio analysis in a narrow window, the present invention eliminates (or at least reduces) the effect of light scattering caused by blood solutes other than the analyte as well as the scattering effects of background and patient-dependent factors (e.g., pigmentation, thickness and vascularization of the skin) that might otherwise interfere with accurate measurements.

It has been discovered that particular advantages can be obtained when closely-spaced data and reference wavelengths are selected, because when greater distances separate the analyte data wavelength from the reference wavelength, the effects of scattering on the measured ratio typically will be larger and more erratic. Thus, having a narrow detection window within which all the measurements are taken can limit the range of variation and, therefore, the effect of these phenomena, yielding a more accurate, determination of in vivo blood-analyte levels.

Furthermore, it has also been discovered that scattering increases as wavelength approaches the visible light range. Therefore, in practice of the invention, two wavelengths are selected as close together as possible, to assure a narrow window, and the window is located at a relatively long wavelength, e.g., over 1000 nm.

For example, to measure glucose levels in a circulating bloodstream within a subject, glucose absorbance data is reliably obtained at about 1600 nm +/− 15 nm, and reliably evaluted when selected in combination with a reflectance reference wavelength in the close by range of 1630-1660 nm, the latter being relatively insensitive to glucose content. In the case of glucose measurement, a reference reading above the 1600 nm data point (e.g., in the 1630 to 1660 nm range) is preferable over a reference measurement below the data point (e.g., in the 1540 to 1570 nm range) because of urea and water measurement peaks at about 1500 nm can cause interference. The absorption of light by other analytes at 1600 nm and in the 1630 1660 range is relatively low, or the differences are small, thereby minimizing interference due to such other analytes.

In the event that problems are encountered in measuring glucose in this range, then a reference reflectance reading may be obtained at about 1300 nm, as an alternative or supplemental reference reading. While the latter reference wavelength is further removed from 1600 nm, and typically will result in lower precision due to increased scattering effects, it provides an alternative or supplemental reference wavelength which will still yield favorable results.

In another example of the invention, cholesterol levels can be measured in a circulating bloodstream within a subject, by obtaining light absorbance data at about 1720 nm +/− 15 nm, or at about 2300 nm +/− 15 nm, in combination with a closely spaced reference wavelength, the latter being relatively insensitive to cholesterol content.

In yet another example of the invention, urea levels can be measured in a circulating bloodstream within a subject, by obtaining light absorbance data at about 1500 nm+/−15 nm, in combination with a closely spaced reference wavelength, the latter being relatively insensitive to urea content.

As used herein the term "near infrared" or "near IR" is intended to encompass light in a spectrum ranging from about 1000 to about 2500 nm, more preferably from about 1300 to about 2300 nm, and, in some instances, most preferably from about 1500 to about 1800 nm.

As used herein the terms "closely spaced" or "narrow window" are intended to describe paired wavelengths for measurement of an analyte, with a first wavelength being chosen proximal to a near infrared (IR) absorption peak for the analyte which varies with concentration of the analyte (the data wavelength) and the a second (reference) wavelength being sufficiently removed from the first so that measurements of light absorption at this second wavelength are relatively insensitive to the concentration of the analyte and yet the second wavelength is sufficiently close to the first wavelength to minimize interference from scattering effects and the like. Typically, the window bracketing these closely spaced wavelengths will be less than about 300 nm and preferably less than about 60 nm wide and, in some instances, more preferably less than about 30 nm wide.

By choosing a data wavelength that is highly specific for a particular analyte (i.e., with no competing nearby absorption peaks), the use of a narrow window also assures that non-analyte absorption effects as well as scattering effects are minimized.

In another aspect of the invention, an analytic apparatus and method are described employing a multi-wavelength illumination source, a wavelength-specific detector array and a reflection ration analyzer. The illumination source illuminates material sample at a plurality of discrete wavelengths selected from the near infrared region, in a narrow window as described above, e.g., less than about 300 nm or preferably less than about 60 nm wide and, in some instances, more preferably less than about 30 nm wide.

The detector array detects the IR light absorbed by the sample, converts the detected light into electrical signals indicative of the intensity of the reflected (or transmitted) light at each selected wavelength. These signal can then be processed by a absorption ratio analyzer. The ratio analyzer then derives a ratio for at least two of the detected wavelengths, for example, in the case of glucose, selecting a reference wavelength at approximately 1630-1660 nanometers and a glucose data wavelength at approximately 1600 nanometers, such that the ratio can be compared with predetermined values to non-invasively detect the concentration of glucose in a subject's circulatory system.

In one particular embodiment of the invention, the illumination source further includes at least two laser diodes, producing light at distinct wavelengths, to illuminate the subject's skin with IR light at both a reference and a data wavelength. This embodiment is particularly well-suited to providing a system for detecting glucose in blood circulating through a surface vein, or in a nailbed of a finger, due to the penetration of near infrared wavelengths of light through human tissue.

The methods of the invention utilizes the observation that analytes differentially absorb near IR light at various wavelengths and that data and reference wavelength can be chosen to quantify the presence of the analyte, non-invasive reflectance or transmittance measurements. For example, a surface vein in a human subject, or a fingernail bed, can be illuminated with light at a first data wavelength, and a non-invasive reading is taken so as to establish a blood analyte level. The vein or bed is also either concurrently or sequentially illuminated with light at a second reference wavelength and a second non-invasive reading is taken, so as to establish a baseline background value. The ratio of these reflectance readings is compared to known (e.g., stored in a look-up table) ratios relating to known analyte levels, and an analyte level is thereby determined.

The present invention is an improvement over the prior art in that it can, with improved accuracy, non-invasively, quickly and easily detect and/or quantify blood analyte levels. In this way, the invention eliminates the problems of non-continuous data, subject discomfort and/or potential exposure to infectious diseases.

The invention will next be described in connection with certain preferred embodiments; however, it should be clear that various additions, subtractions and modifications can be made without departing from the spirit or scope of the invention. For example, although the invention is illustrated in connection with a blood analysis system, various alternative embodiments can also be devised. Furthermore, while reflectance measurements are primarily discussed, transmittance measurements may be employed in a similar manner as an alternative in practice of the invention.

Although the illustrated embodiment shows a system with a fiber optic bundle for delivery of six distinct wavelengths of light, it should be clear that the number of interrogation wavelengths, the size and shape of the sampling head, and the means for transmitting the light to and from the sample, can be varied to meet particular needs and applications. For example, in monitoring blood sugar levels, as few as two wavelengths may be used to measure the glucose concentration. Moreover, a single fiber can be used for transmission and detection of multiple interrogation wavelengths. Additionally, although lasers are described as preferred light sources, other illumination means, including non-coherent, discrete wavelength light sources, can be employed.

DETAILED DESCRIPTION

Figure 1:
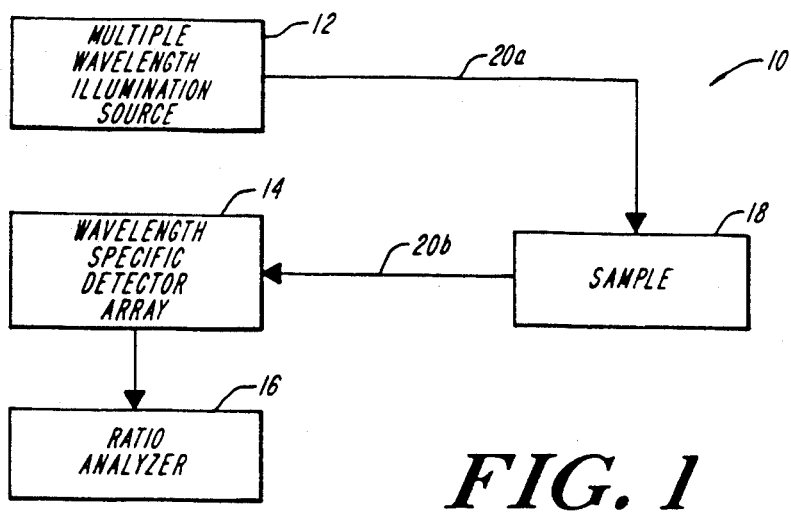
FIG. 1 is a schematic block diagram of an analytic apparatus according to the invention.

In FIG. 1, a schematic block diagram of an analytic apparatus 10 according to the invention is shown. Apparatus 10 includes a multiple wavelength illumination source 12, a wavelength specific detector array 14, and a reflection ratio analyzer 16.

Illumination source 12 can be a single, multiwavelength laser diode or a series of discrete diode elements, each emitting a distinct wavelength of light selected from the near infrared region to illuminate a blood sample 18 via optical path 20a. In some applications, illumination source 12 can be a broadband near IR emitter, emitting both the data and reference wavelengths as part of a broadband interrogation burst of IR light or radiation.

Detector array 14 detects light reflected (or transmitted) by sample 18 through optical path 20b. The detector array 14 converts the reflected light into electrical signals indicative of the degree of absorption light at each wavelength and transfers the converted signals to the absorption ratio analyzer 16. Analyzer 16 processes the electrical signals and derives an absorption (e.g., a reflection or transmittance) ratio for at least two of the wavelengths. Analyzer 16 then compares the calculated ratio with predetermined values to detect the concentration and/or presence of the analyte in the blood sample 18.

Figure 2:
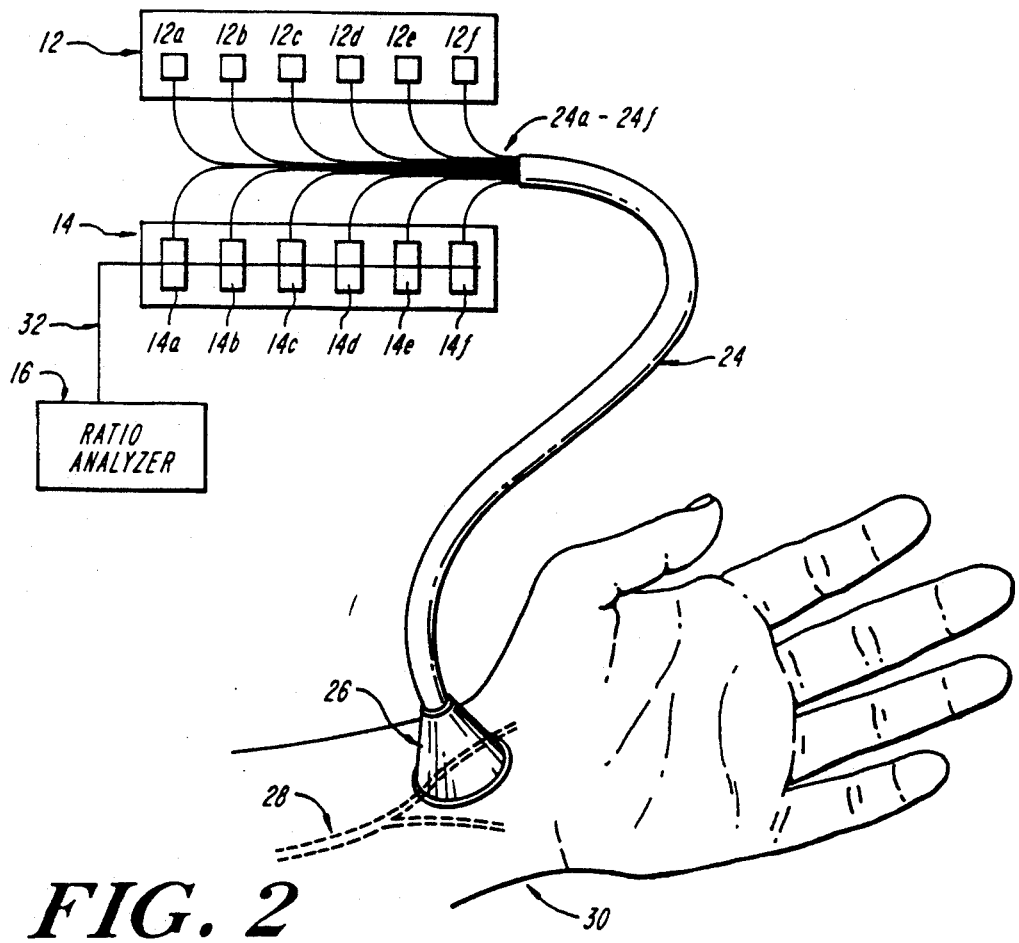
FIG. 2 is a schematic diagram of the apparatus according to the invention particularly adapted for non-invasive detection of glucose in a subject's blood.

An embodiment of analytic apparatus 10 particularly adapted to provide reflective measurements of analytes in blood circulating through a surface vein is shown in FIG. 2. As can be seen from FIG. 2, laser diode elements 12a-12f comprise a multiple wavelength illumination source 12, which provides light at a series of skin penetrating wavelengths. Diode elements 12a-12f can each transmit a predetermined wavelength of light via corresponding optical fiber elements 24a-24f and sampling head 26, to vein segment 28 of wrist 30. (Alternatively, light at various wavelengths can be emitted by one multiple-wavelength laser diode and transmitted via a single optical fiber.) The discrete wavelengths of laser light automatically pass through the tissue of wrist 30 and illuminate the blood circulating in surface vein 28.

For example, at least one of the diode elements 12a-12f can transmit interrogating radiation in a wavelength range of about 1600 nm in order to obtain glucose concentration data, and another of the diode elements 12a-12f can transmit radiation in at about 1630-1660 nm, or about 1540-1570 nm, to obtain qlucose reference measurements. In some instances, it may also be preferable to take at least one further glucose reference reading (e.g., at about 1300 nm) using another of the diode elements 12a-12f to provide additional baseline data for analyte discrimination. Other diode elements can be dedicated to the measurement of other analytes (such as cholesterol, urea or ureic acid, using similar pairs of closely spaced data and reference wavelengths, as described above).

Following irradiation by the diode elements 12a-12f, a fraction of the transmitted light is reflected back from the blood circulating in surface vein 28 along optical fiber elements 24a-24f. (In one embodiment, each optical fiber element 24a-24f carries a reflected light signal having the same wavelength as the light originally transmitted along it.) Diode detectors 14a-14f receive the reflected light from the optical fiber elements 24a-24f and convert these light waves into a series of electrical signals indicative of the intensity of each of the reflected wavelengths of light received from surface vein 28. For example, if laser diode element 12a originally transmitted light of wavelength 1595 nm (a glucose data measurement wavelength) along optical fiber element 14a, then optical fiber element 14a can also carry reflected light of wavelength 1595 nm back to diode detector element 22a.

As shown in FIG. 2, diode detector elements 14a-14f transmit the electrical signals indicative of the intensity of the reflected light to reflection ratio analyzer 16 along electrical connection 32. Analyzer 16 compares the electrical signals received from diode detector elements 14a-14f to derive a reflectance ratio for at least two of the transmitted wavelengths of light, such that the ratio can be compared to predetermined values to detect the presence of glucose in the blood flowing through vein 28. Analyzer 16 then can be employed to determine the presence and concentration of glucose, alone or along with other blood analytes.

Figure 3:
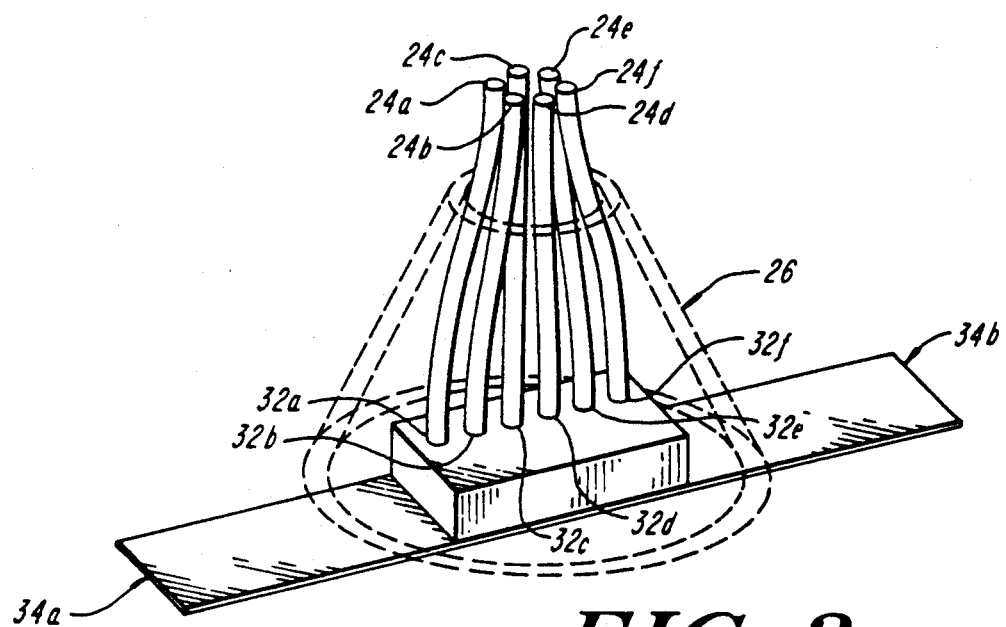
FIG. 3 is a detailed view of a sampling head assembly of the apparatus of FIG. 2.

FIG. 3 shows a more detailed view of the sampling held 26 of FIG. 2. As can be seen from FIG. 3, optical fiber elements 24a-24f of optical fiber bundle 24 are adapted to extend through a corresponding set of holes 32a-32f in the sampling head 26, thus, facilitating alignment of optical fiber elements 24a-24f along a surface vein or other vascular region. Sampling head 26 also comprises taping flanges 34a and 34b located at opposed ends of sampling held 26, providing a means for affixing sampling held 26 above the surface.

Figure 3A:
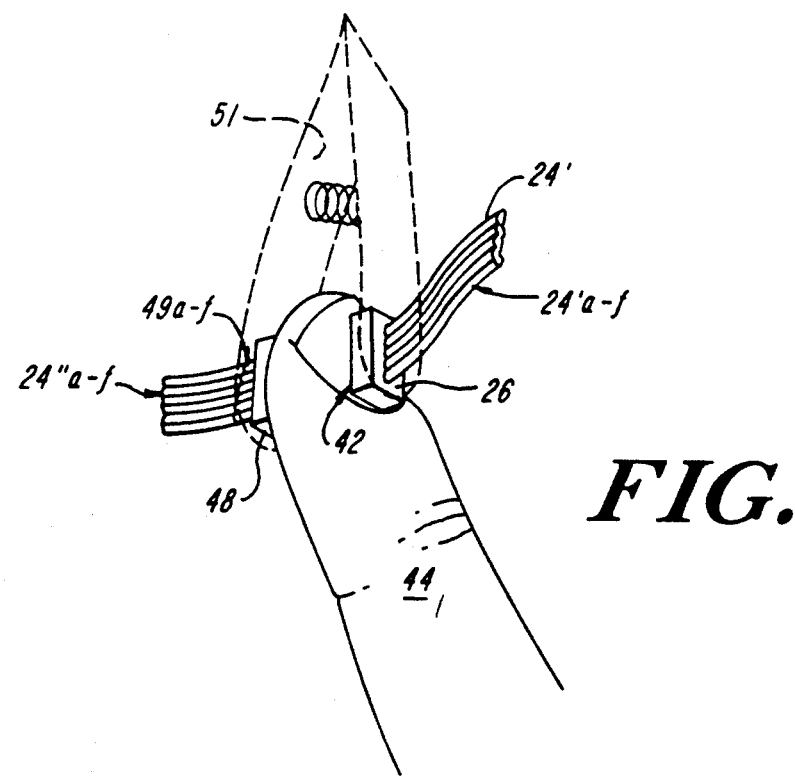
FIG. 3A is a schematic view of an alternative apparatus according to the invention.

FIG. 3A shows an alternative embodiment of a sampling held 26 of FIG. 2. Optical fiber elements 24'a-f optical fiber bundle 24' coupled to source 12 are adapted to extend through a corresponding set of holes in the sampling head 26A, thus facilitating alignment of the optical fiber elements at the surface 42 of a finger 44 immediately above a nailbed 46. The light from fibers 24'a-f is transmitted through the finger and absorption is measured by applying a detector 48 on the opposite side of the finger. The detector 48 can employ a corresponding series of optical fibers 24"a-f and, optionally, a corresponding set of wavelength-specific filters 49 a-f, as shown, or, in a more simple embodiment, a broadband detector can be used and rely, for example, on sequential emissions of specific interrogation wavelengths by the illumination means.

The sampling head 26A and detector 48 can be attached to the fingertip by a clip 51, as shown, or by straps located at opposed ends of sampling head 26A, in a manner similar the attachment means of FIG. 3, to provide a means for affixing the apparatus about the finger. (In other transmittance measuring embodiments, the sampling head 26A and detector 48 can be disposed in other locations as well, such as an earlobe, toe or the like.)

Figure 4:
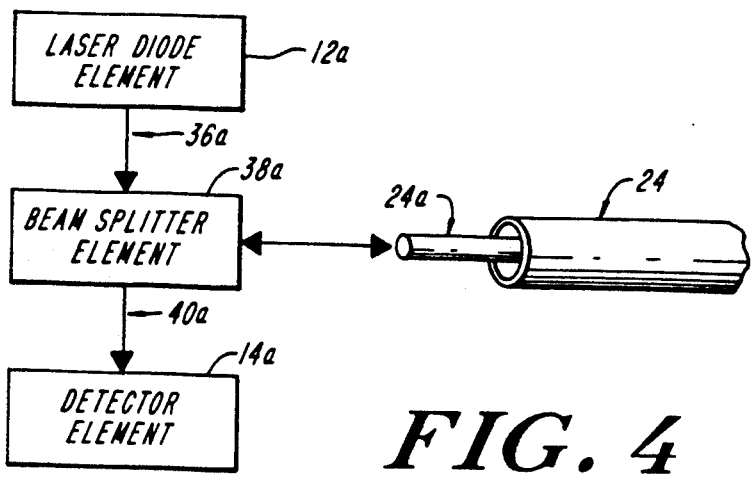
FIG. 4 is a more detailed illustration of an individual optical fiber and its connection to an illumination source and a detector element according to a reflection mode embodiment of the invention.

FIG. 4 is a more detailed illustration of an individual optical fiber 24a and its connection to an illumination source 12a and a detector element 14a in a reflection-mode analysis system according to the invention. Since each of optical fiber elements 24a-24f is identically adapted, only optical fiber element 24a is shown. Laser diode element 12a is connected to optical fiber element 24a via optical fiber element 36a through optical splitter 38a. Diode detector element 14a is connected to optical fiber element 24a via optical fiber element 40a, also through optical splitter 38a. Optical splitter element 38a and corresponding elements 38b-38f, not shown) enable dual usage of optical fiber elements 24a-24f so that the light emitted by laser diode elements 12a-12f and not absorbed by the tissue sample travels along the same optical fiber elements 24a-24f.

Figure 5:
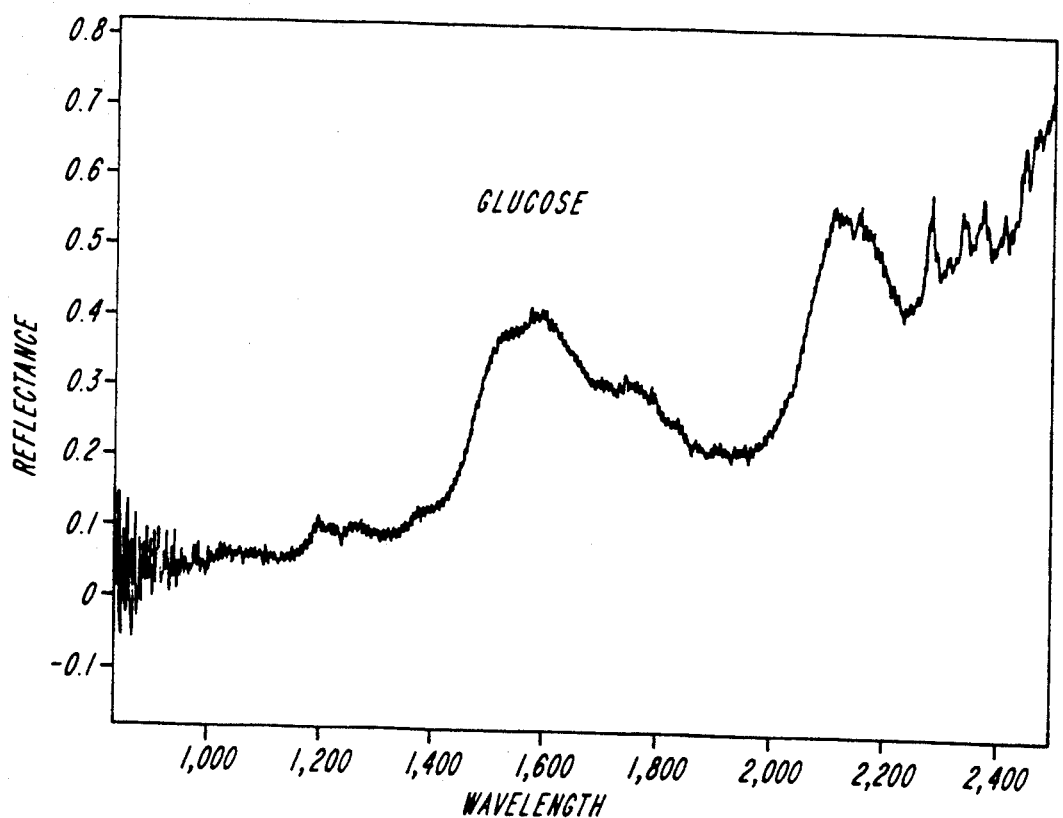
FIG. 5 is a graph of the reflectance spectrum of glucose, illustrating the analytical techniques of the present invention.

For example, in blood sugar analysis, it has been observed that glucose has peaks in the near infrared that are in well-defined spectral regions and differentiable from the blood background. FIG. 5 is a graph of the reflectance spectrum of glucose. The wavelength of the source light is shown along the x-axis and reflectance (in terms of log (1/R), where R is the intensity of the light reflected back from the blood) is shown along the y-axis in arbitrary units. As shown in FIG. 5, glucose shows a strong absorbance peak at about 1600 nm.

Figure 6:
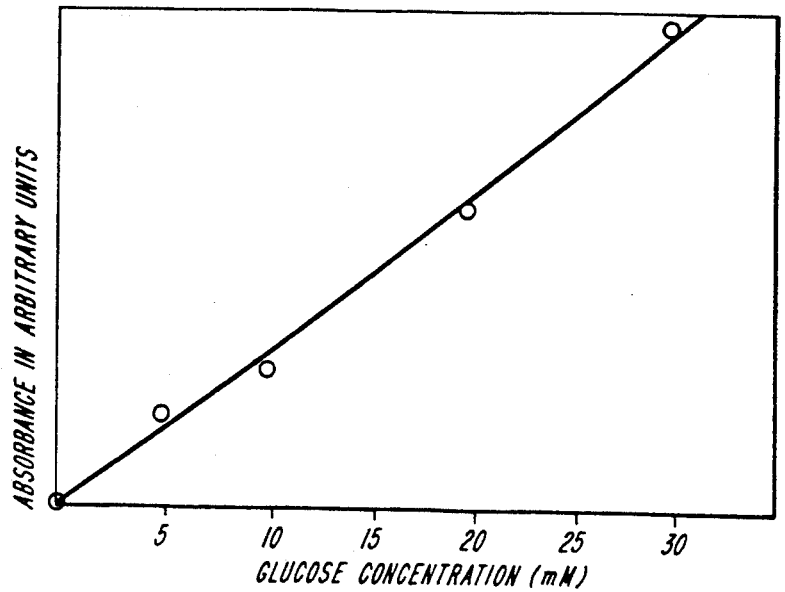
FIG. 6 is a graph of absorbance versus glucose concentration for illumination at 1586 nm for several concentrations of glucose.

FIG. 6 is a graph illustrating the principles of the present invention applied to glucose concentration measurement. FIG. 6 is a plot of absorbance of infrared radiation at about 1600 nm versus actual concentrations of glucose in an aqueous solution. The absorbance measurements were taken by irradiating samples through an excise dog artery wall to simulate in vivo conditions. As can be seen from the graph, the measured absorbance provides an accurate determination of glucose concentration in a linear fashion and over a wide range of concentrations.

The present invention is based on the recognition that there is a general class of scattering phenomena and absorption by other analytes which can effect reflectance (or transmittance) readings. It is further recognized that the particular combination of wavelengths selected for rationing can effect detection accuracy. This is true because selection of a narrow window for obtaining all reflectance/absorbance data has the benefit of canceling out the effect of light scattering and non-specific absorption. These scattering phenomena are principally due to size issues, i.e., big molecules making up the skin, the blood, and the cells themselves. Other artifacts in the detected reflectance signals can arise from skin pigmentation and gross variations in blood constitution from patient to patient.

Figure 7:
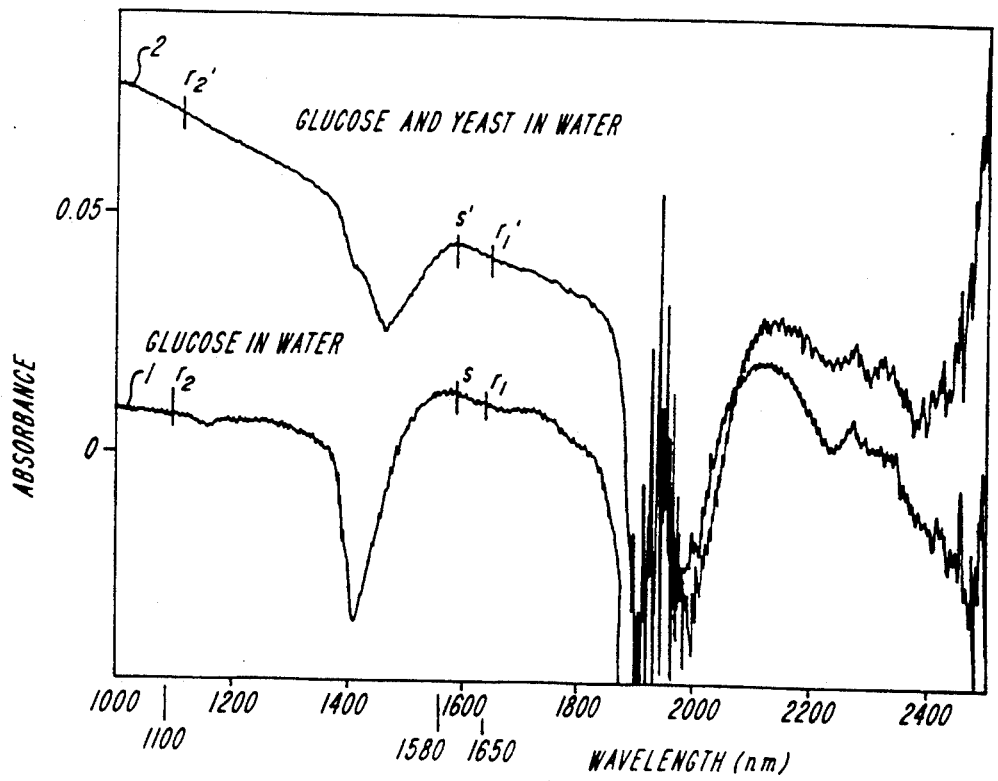
FIG. 7 is a graph of glucose absorbance in arbitrary units versus wavelength from about 1100 to 2500 nm, for two samples (curve 1 and 2) having the same concentration of glucose in water, with one sample (curve 2) also including a scattering analyte.

FIG. 7 is a graph of glucose absorbance for two aqueous samples having the same amount of glucose, but one loaded with a scattering analyte. The data is measured over a range of infra-red illumination of about 1000–2500 nm. Curve 1 shows absorbance for glucose alone in water (no scatterer), and curve 2 shows the absorbance characteristics for glucose and a scatterer (yeast) in water. The wavelength of the source light is shown along the x-axis ranging from about 1000–2500 nm. The absorbance of light is shown along the y-axis. For curves 1 and 2, respectively, the glucose absorbance value (s, s') for glucose is indicated at about 1600 nm and then an absorbance reference value is indicated at about 1650 nm (rl,rl') and at about 1100 nm (r2,r2').

The effect of scattering is demonstrated from FIG. 7 by comparing the divergence of the reference signal from the data signal for each reference datum, for each curve. For glucose in water (curve 1), the first reference signal (rl) diverges from the glucose absorbance data signal (s) by about 0.0025 units, and the second reference signal (r2) diverges from the data signal (s) by about 0.0048 units. For glucose and yeast in water, the first reference signal (rl') diverges from the data signal (s') by about 0.0022 units, and the second reference signal (r2') diverges from the data signal (s') by about 0.0284 units, approximately an order of magnitude larger difference than that obtained using a closer reference wavelength. In particular, it should be noted that the closer reference differences ($r_1-s_1$ and $r'_1-s'_1$) deviate insignificantly in the two systems despite the large differences in scattering capacity.

This experiment therefore demonstrates not only the substantial variation in readings caused by the presence of scatterers in a blood sample compared to readings for samples without scatterers, but also shows that by selecting the reflectance reference signal wavelength very close to the glucose absorbance data signal wavelength minimizes the effect of scattering. Similar results are obtainable for other analytes, such as cholesterol, urea and uric acid.

Furthermore, given that scattering increases as wavelength decreases, we have selected a preferred narrow window, with the glucose absorbance wavelength at about 1600 nm and the reference signal taken at about 1630–1660 nm. This selection therefore reduces scattering by selection of relatively long wavelengths and by the narrowness of the 1600–1660 nm window. These selected values exploit the forgoing properties of glucose by taking the ratio of light reflected from blood at a first near infrared wavelength where glucose absorption is minimal, and at a second, wavelength where reflectance will be dependent on the concentration of glucose present in the irradiated region, with minimized effect of light scattering on the subsequent absorption rationing.

Figure 8:
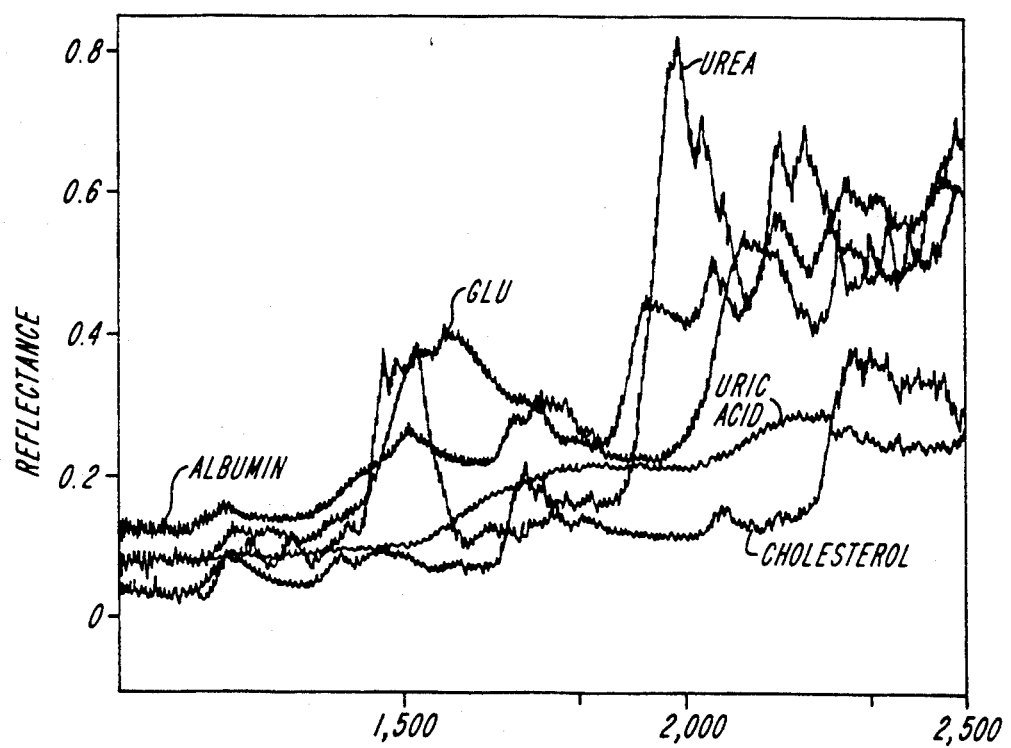
FIG. 8 is a graph of absorbance exhibited by albumin, glucose, urea, uric acid and cholesterol in a blood sample illuminated over the range of 1000 to 2500 nm.

FIG. 8 is a graph of absorbance exhibited by albumin, glucose, urea, uric acid and cholesterol in a blood sample illuminated over the range of 1000 to 2500 nm, and provides another analytical example of the invention, namely, an analysis for cholesterol in blood. At about 1720 nm and 2300, cholesterol reaches an absorption peak, while the other analytes are in a more gradual mode. After determination of the level of other analytes of interest (albumin, uric acid, glucose, urea) a subtractive process can be used to obtain the detection signal for glucose, cholesterol or any other analyte of interest.

The cholesterol data signal is obtained and is compared to the reference wavelength and a ratio is obtained by the rationing described above, and then the ratio is compared to data stored in a look-up table to obtain a cholesterol reading for the subject. If a narrow detection window of about 100 nm is used, e.g., 1720 compared to 1620 or 1820, for example, this has the benefit of substantially reducing scattering effects.

Thus, the present invention benefits from the recognition that there is a general class of scattering phenomena which can effect reflectance readings. These scattering phenomena are principally due to size issues, i.e., big molecules making up the skin, the blood, and the cells themselves. Other artifacts in the detected reflectance signals can arise from skin pigmentation and gross variations in blood constitution from patient to patient.

Furthermore, given that scattering increases as wavelength shortens, we have selected a preferred narrow window, with the cholesterol absorbance wavelength at about 1720 nm or 2300 nm. The invention can therefore reduce scattering by selection of relatively long wavelengths and by selection of as narrow a window as possible. Nevertheless, where necessity dictates, such as where other analytes are present, other wavelengths in the near infrared range may also be used in useful practice of the invention.

In view of the above, these selected values exploit the foregoing properties of cholesterol by taking the ratio of light reflected from or transmitted by blood at a reference near infrared wavelength where cholesterol absorption is minimal, and at a data near infrared wavelength where reflectance or transmittance will be dependent on the concentration of cholesterol present in the irradiated region, with minimized effect of light scattering on the subsequent reflectance rationing.

The foregoing embodiments have been described with respect to reflectance; however, they are equally operable with measurement of transmittance.

The site of application of the invention has been described with respect to a vein, but also may be applied to the bed of a fingernail or other easily accessible areas where blood flow is adequate.

Light sources, such as laser diodes or light-emitting diodes, at the preferred wavelengths disclosed herein may be used, either custom designed or as tuned or filtered in a conventional manner. As indicated above, the invention may be embodied in other specific forms without departing from the spirit or the essential characteristics thereof. The present embodiment is to be considered as illustrative and not restrictive. The scope of the invention is indicated by the appended claims, rather than by the foregoing description, and all changes which come within the meaning and range of equivalent of the claims are therefor intended to be embraced therein.

What is claimed is:

1. A blood-analyte detection apparatus comprising:
   infrared illumination means for non-invasively illuminating an in vivo blood sample in a patient at least two wavelengths in the near infrared spectrum;
   detector means for non-invasively measuring light absorbed by said sample at least a first data wavelength and a second reference wavelength, and for converting said detected light into electrical signals, said signals being indicative of the intensity of said detected light at each wavelength;
   the detector means further characterized as measuring light absorption at two closely-spaced wavelengths said first and second wavelengths spaced by less than about 60 nanometers in order to minimize inference from extraneous factors.

2. The apparatus of claim 1 wherein the illumination means is broadband infrared emitter.

3. The apparatus of claim 1 wherein the illumination means comprises a plurality of discrete IR radiation sources emitting light at different wavelengths in the near infrared spectrum.

4. The apparatus of claim 1 wherein the illumination means emits at least two wavelengths of infrared radiation within a spectrum ranging from about 1000 to about 2500 nm.

5. The apparatus of claim 1 wherein the illumination means emits at least two wavelengths of infrared radiation within a spectrum ranging from about 1300 to about 2300 nm.

6. The apparatus of claim 1 wherein the illumination means emits at least two wavelengths of infrared radiation within a spectrum ranging from about 1500 to about 1800 nm.

7. The apparatus of claim 1 wherein said detector means detects the reflectance of said light upon said sample.

8. The apparatus of claim 1 wherein said detector means detects the transmittance of said light by said sample.

9. The apparatus of claim 1 wherein the detector further comprises a plurality of wavelength specific filters.

10. The apparatus of claim 1 wherein said first and second wavelengths are separated by less than about 30 nm.

11. The apparatus of claim 1 wherein one of said wavelengths is about 1600 nm for generating an analyte data signal and another of said wavelengths is about 1630-1660 for generation of a reference signal.

12. The apparatus of claim 1 wherein one of said wavelengths is about 1300 nm for generating a reference signal.

13. The apparatus of claim 1 wherein the apparatus further comprises an analyzing means for receiving and comparing said electrical signals to derive a detection ratio for at least two of said wavelengths, such that said ratio can be compared with predetermined values associated with known blood-analyte concentrations so as to detect the analyte level in said sample.

14. A method for detecting an analyte in a blood sample, comprising the steps of:
   illuminating a source of blood non-invasively through the tissue of a subject at a plurality of wavelengths within a narrow window selected in the near infrared spectrum;
   detecting light effected by said blood and converting said detected light into electrical signals indicative of the intensity of said effected light at a plurality of wavelengths selected from the near infrared spectrum, including a first data wavelength and a second reference wavelength separated by less than about 60 nanometers;
   analyzing said electrical signals to derive a ratio for at least two of said wavelengths; and
   comparing said ratio to a predetermined value to detect the presence of an analyte in said blood.

15. The method of claim 14 wherein said first and second wavelengths are separated by less than about 30 nm.

16. The method of claim 14 wherein said detected light is a measure of the reflectance of said blood.

17. The method of claim 14 wherein said detected light is a measure of the transmittance of said blood.

18. The method of claim 14 wherein said tissue is skin.

19. The method of claim 14 wherein said tissue is in a nailbed.

20. The method of claim 14 wherein said tissue includes a vein.

* * * * *